US009402597B1

(12) United States Patent
Castellanos

(10) Patent No.: US 9,402,597 B1
(45) Date of Patent: Aug. 2, 2016

(54) MOBILE VASCULAR HEALTH EVALUATION PROCESSES

(71) Applicant: Alexander F. Castellanos, Templeton, CA (US)

(72) Inventor: Alexander F. Castellanos, Templeton, CA (US)

(73) Assignee: Alexander Francis Castellanos 2002 Trust, Templeton, CA (US)

( * ) Notice: Subject to any disclaimer, the term of this patent is extended or adjusted under 35 U.S.C. 154(b) by 592 days.

(21) Appl. No.: 13/733,079

(22) Filed: Jan. 2, 2013

Related U.S. Application Data

(60) Provisional application No. 61/694,728, filed on Aug. 29, 2012.

(51) Int. Cl.
*A61B 8/12* (2006.01)
*A61B 5/0205* (2006.01)

(52) U.S. Cl.
CPC .............. *A61B 8/12* (2013.01); *A61B 5/0205* (2013.01)

(58) Field of Classification Search
CPC ................................ A61B 8/12; A61B 8/0205
See application file for complete search history.

(56) References Cited

U.S. PATENT DOCUMENTS

| 2002/0183599 | A1* | 12/2002 | Castellanos | A61B 5/02007 600/300 |
| 2004/0127798 | A1* | 7/2004 | Dala-Krishna et al. | 600/450 |
| 2007/0276270 | A1* | 11/2007 | Tran | 600/508 |
| 2013/0053655 | A1 | 2/2013 | Castellanos | |

OTHER PUBLICATIONS

Keller et al., Noninvasive angiography for the diagnosis of carotid artery disease using Doppler ultrasound (carotid artery Doppler), Stroke. 1976;7:354-363.*
U.S. Appl. No. 13/598,371, filed Aug. 29, 2012, Final Office Action.
U.S. Appl. No. 13/598,371, filed Aug. 29, 2012, Office Action, May 26, 2015.

* cited by examiner

*Primary Examiner* — Bo J Peng
(74) *Attorney, Agent, or Firm* — Hickman Palermo Becker Bingham LLP

(57) ABSTRACT

In an embodiment, a data processing method comprises receiving, from a portable physiological measuring device configured for temporary attachment to a human body, data representing one or more physiological metrics or parameters of the body; receiving, from one or more Doppler vascular sensors configured for temporary attachment to peripheral artery locations of the body and a portable Doppler vascular signal measuring device coupled to the Doppler vascular sensors, vascular function information for the body; determining medical condition data indicating one or more medical conditions of the patient based on analysis and correlations of the vascular function information and the patient physiological metrics; generating and providing output records specifying one or more of: recommendations for actions that an individual or healthcare provider should take in response to the recommendations or parameters; or one or more reports, animations or figures; wherein the method is performed by one or more computing devices.

30 Claims, 5 Drawing Sheets

US 9,402,597 B1

MOBILE VASCULAR HEALTH EVALUATION PROCESSES

CROSS-REFERENCE TO RELATED APPLICATIONS

Benefit Claim

This application claims the benefit under 35 U.S.C. §119 (e) of provisional application 61/694,728, filed Aug. 29, 2012, the entire contents of which is hereby incorporated by reference as if fully set forth herein.

FIELD OF THE INVENTION

The present disclosure generally relates to medical devices and medical diagnostic methods, and more specifically relates to computer program applications and techniques for assessing health conditions of elements of the vascular system.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

In humans, negative vascular condition has been associated with or is known to be symptomatic with a variety of serious diseases including coronary artery disease, hypertension, stroke, kidney disease, muscular skeletal disorders, nervous system disorders, respiratory diseases, cardiac rhythm disease, diabetes, and others. For example, reduced elasticity of the coronary arteries may indicate the presence of plaque on the walls of the arteries and may contribute to myocardial infarction. Vascular function information also may be useful in early recognition of sepsis, hypertension, hypotension, or respiratory dysfunction, and cardiac rhythm dysfunctions. Accurate measurements of the elasticity, thickness, and mechanical performance of blood vessels in conducting blood flow may permit better evaluation of diseases that are associated with negative vascular health and recommendation of a variety of therapies.

However, in the state of the art, vascular measurements typically require elaborate equipment and can only be performed in a clinical setting on a periodic basis. For example, one typical method involves using Doppler sonography systems to obtain acoustic readings from the peripheral principal arteries from one or more body locations, such as the ankles. Most systems are large, expensive, and normally capable of use only in a medical office. Other vascular systems try to measure vascular wall thickness, so that it is difficult to accurately measure abnormal plaque from normal artery wall. Further, these systems normally are not integrated with other valuable measures of personal health.

Devices are available that measure vital signs, blood glucose, gases in the body, respiratory activity, cardiac rhythm and other aspects of physiology. For example, smartphone applications or "apps" are available to enable an individual to take their pulse using a smartphone, and other apps can take pictures of food and provide readouts of food contents and calories. However, these measurements and apps may be incapable of integrating with other valuable health information or providing a global assessment, involving vascular function, of healthy or unhealthy status.

SUMMARY OF THE INVENTION

The appended claims may serve as a summary of the invention.

BRIEF DESCRIPTION OF THE DRAWINGS

The present invention is illustrated by way of example, and not by way of limitation, in the figures of the accompanying drawings and in which like reference numerals refer to similar elements and in which.

DESCRIPTION OF EXAMPLE EMBODIMENTS

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Overview of Example Mobile Measurement Devices

Figure 2:
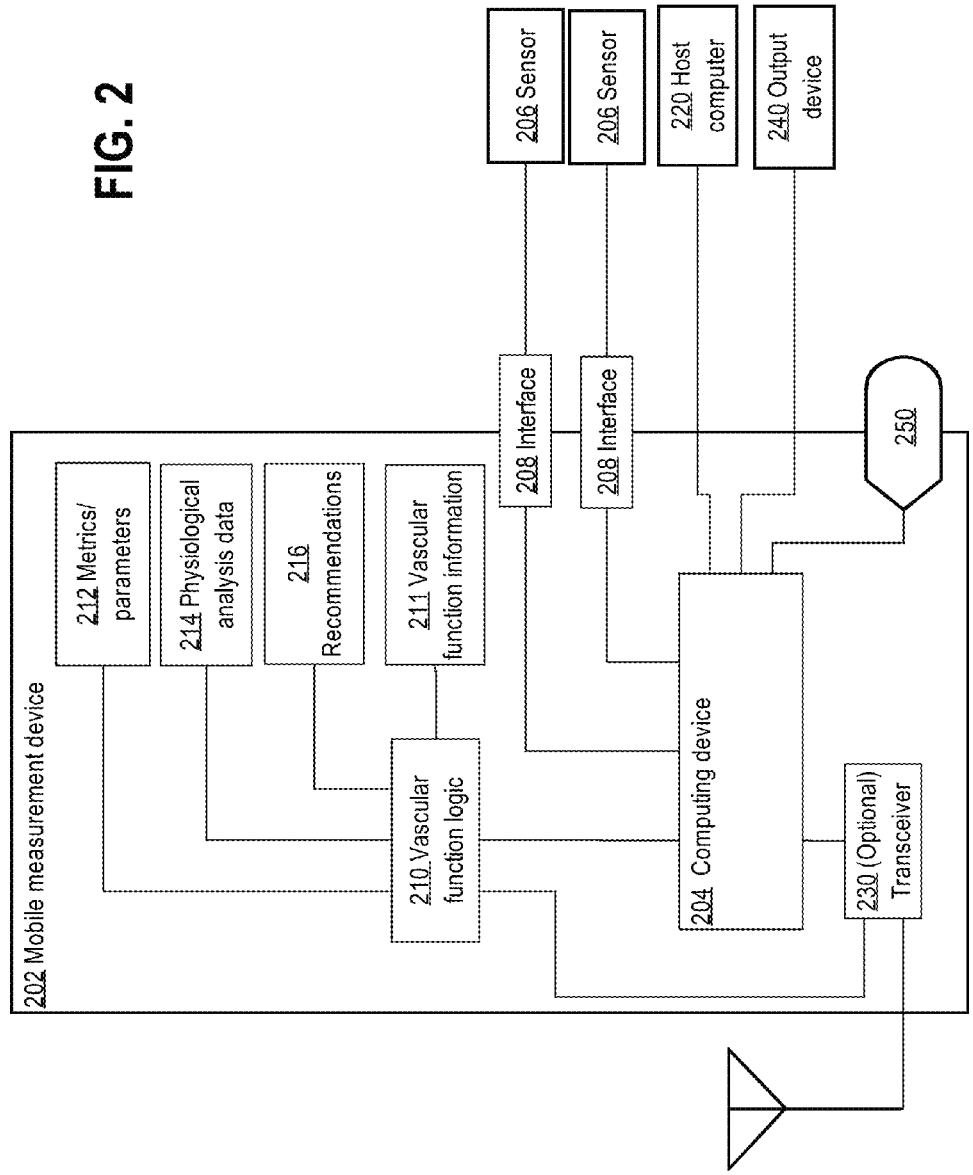
FIG. 2 illustrates an example mobile measurement device.

In an embodiment, a mobile measurement device is configured to process information from the environment and human physiology and anatomy. FIG. 2 illustrates an example mobile measurement device. In an embodiment, the mobile measurement device 202 comprises: a computing device 204; one or more sensors 206 that are coupled to the computing device using one or more corresponding compatible digital interfaces 208; and vascular function logic 210 encoded with instructions which when executed perform determining and storing vascular function information 211 and one or more of: values of metrics or parameters 212; physiological analysis 214 of the parameters and the vascular function information; recommendations 216 for actions that an individual or healthcare provider should take in response to the recommendations or parameters.

In various embodiments, the computing device 204 comprises any of: a smartphone; a tablet computer; a laptop computer or other personal computer; a workstation; a watch computer; a ring-mounted computer; an active steering wheel of a motor vehicle; a hat-mounted computer; a helmet-mounted computer; an eyewear-mounted computer. In other embodiments, the computing device 204 comprises or is integrated with any of: a body garment such as a short, swimsuit, vest, shorts or shoes.

In various embodiments, the sensors 206 comprise at least one of the following: an ultrasound sensor configured to acoustically measure structure, performance or other metrics associated with a blood vessel or other element of the vascular system and to cooperate with the program logic to provide output waveform data representing acoustic measurements of blood flow in a blood vessel, and provide vascular structure or performance metrics 212 based on bidirectional vascular waveform analysis. In an embodiment, one of the sensors 206 or the vascular function logic 210 perform bidirectional waveform Doppler ultrasound analysis that can measure or indicate the elasticity of one or more blood vessels. In an embodiment, the vascular function information 211 comprises or is based on the bidirectional waveform Doppler ultrasound analysis.

In various embodiments, the sensors 206 comprise one or more of any of the following: an infrared sensor, crystal technology sensor, sensors configured for use with augmented reality technology, auto-fluorescence sensors, or light-based physiological monitor; a blood pressure sensor; a pulse sensor; a respiratory rate sensor comprising, for example, one or more chest patches, wrist patches, and/or chest straps; a body temperature sensor; an oxygen absorption sensor; a carbon dioxide sensor; a nitric oxide sensor; a blood glucose sensor; a sensor of electrolytes, nutrients in the circulation, or other metrics; one or more contact lenses configured to measure capillary blood flow; a flow meter; a spirometer; a mouthpiece. In an embodiment, at least one of the sensors 206 is configured to sense and store at least one measurement relating to vascular structure, status or performance. Thus, as alternatives to using ultrasound as a form of energy for sensing, in some embodiments sensors that use infrared spectroscopy, auto-fluorescence, crystal technology, augmented reality technology, and other forms of energy or radiation may be used to obtain vascular waveforms for analysis.

In various embodiments, the vascular function logic 210 comprises one or more of any of the following: non-volatile random access memory (NVRAM); flash memory; an application-specific integrated circuit (ASIC); a field programmable gate array; read-only memory (ROM) including any of electrically erasable ROM (EEROM) or electrically programmable ROM (EPROM); disk storage; any of which may be configured with stored program instructions that are arranged to perform the processes that are further described herein. Wireless devices such as wireless probes may be used as sensors 206.

In various embodiments, the vascular function information 211 provides metrics, reports, or values that indicate overall health attributes of blood vessels or other components of the vascular system, or particular attributes of blood vessels or other components of the vascular system. Examples of attributes include elasticity of vascular walls; thickness of vascular walls; and an indication of whether a heart pulse cycle results in one, two, or three elastic responses of the vascular walls; presence or amount of plaque formation on the vascular walls.

In various embodiments, the vascular function information 211 includes phenotypic, genotypic, proteomic, and/or neural process information such as weight, blood pressure, cholesterol, genetic characteristics/diseases, biofeedback from the nervous system, etc.

In various embodiments, the vascular function information 211 may be used to generate, using vascular function logic 210 or other program logic, one or more reports, recommendations 216, or protocols based on the vascular function information. Recommendations 216 may collectively and broadly represent reports and protocols as well as recommendations. In various embodiments, the reports, recommendations or protocols may comprise any of the following: a status report on vascular function; a list of options for medical intervention in the patient based on medical standards of practice based on one or more medical indications represented in the vascular function information; reports or recommendations suggesting sepsis, hypertension, hypotension, respiratory dysfunction, kidney function, heart rhythm, hydration level; a protocol for exercise; a protocol for sports performance; a protocol for patient lifestyle or changes in lifestyle; a protocol for patient stress management; a report of recommendations, or the expected effects of, any of several aspects of treatment including but not limited to hydration, nutrition, exercise, supplements, and medications.

In various embodiments, the mobile measurement device 202 may be configured to directly generate the vascular function information 211, and the one or more reports, recommendations, or protocols based on the vascular function information. Alternatively, the mobile measurement device 202 may be activated or used in a clinical setting such as an emergency room, hospital ward or medical office. The mobile measurement device 202 also may be used or activated in non-clinical settings such as during driving a car, during exercise, during sleep, and during other activities. For example, in any of these embodiments, the mobile measurement device 202 may internally generate the vascular function information 211 and also provide logic for interfacing with an external host computer 220 to download the vascular function information; on the host computer, stored program logic may be configured to generate the one or more reports, recommendations, or protocols based on the vascular function information.

In this manner, the mobile measurement device 202 provides a useful interface between the patient and the medical office; the device may be used to collect a variety of physiological metrics from an individual, including at least one measurement of vascular structure, status or performance, which are then downloaded from the device to the host computer 220. After downloading, program logic on the host computer 220 may be used to generate the one or more reports, recommendations, or protocols for disease intervention based on the vascular function information. Data collected over time can be used to better understand factors influencing the cardiovascular system.

Alternatively, after downloading data from the mobile measurement device 202, an independent measurement of at least one measurement of vascular structure, status or performance is performed in association with the host computer. For example, in one approach, an individual uses the mobile measurement device 202 to monitor any of the physiological metrics described above, then downloads the metrics and transfers or provides the metrics to a healthcare provider via host computer 220. In a clinical setting or quasi-clinical setting, the healthcare provider may use a conventional Doppler vascular sensor to capture an acoustic profile of the vascular performance of the same individual; for example, the healthcare provider could perform a Doppler vascular test of the peripheral arteries. The resulting acoustic waveform data may be combined with the metrics that have been downloaded from the patient's mobile measurement device 202 and, under control of program logic at the host computer 220, used to generate the one or more reports, recommendations, or protocols. In various embodiments, the patient may transfer or provide the metrics to the healthcare provider by any of the following: connecting the mobile measurement device 202 to a personal computer that is owned or operated by the patient, downloading a data file from the device, and streaming, e-mailing or uploading the data file to the healthcare provider; going to the premises of the healthcare provider, connecting the device to a host computer that is owned or operated by the healthcare provider, downloading a data file from the device to the host computer.

In various embodiments, the sensors 206 may comprise units that can detect activity of the nervous system either centrally or peripherally. For example, waveform data from an electroencephalogram (EEG) unit may reveal brain activity that can be correlated to vascular waveform data to identify progress in therapeutic goals and/or the condition of the vasculature.

In various embodiments, the data from sensors 206 may be combined with results or detections of blood test measurements for substances such as cortisol, cholesterol, triglycerides, epinephrine, asymmetrical dimethyl argenine. In various embodiments, the data from sensors 206 may be combined with results or detections of urinalysis to identify blood glucose, proteins, ketone, or blood in the urine, and specific gravity of urine. Values obtained from any of the foregoing measurements or units can be correlated to vascular waveform data to identify progress in therapeutic goals and/or the condition of the vasculature.

Unlike prior approaches, the integration of physiological monitoring metrics with information about vascular function, obtained either in a clinical setting or directly from the monitoring device, enables generating improved overall health assessments or health status information. Further, reports in the embodiments herein provide an explanation of the effect of all the measured physiological functions on vascular health, or overall health. Embodiments typically integrate and incorporate at least one vascular study or vascular analysis, so that an evaluation of vascular health is an integral aspect of the reporting and recommendations herein.

Figure 3:
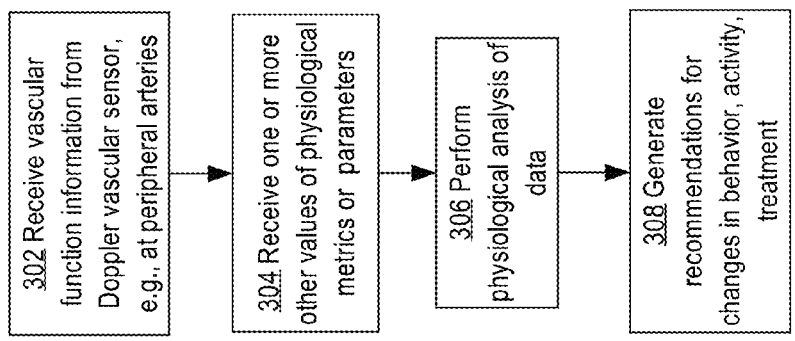
FIG. 3 illustrates an example process of generating recommendations based at least in part on vascular function information.

FIG. 3 illustrates an example process of generating recommendations based at least in part on vascular function information. At step 302, vascular function information is received from at least one Doppler vascular sensor that is used, for example, at the peripheral arteries, such as at the ankles, wrists, as well as the neck, chest or other site. One of the sensors 206 typically is a Doppler vascular sensor in an embodiment and obtains the vascular function information 211, which may be received at step 302 and stored in the form of raw sensor data or as a rendered waveform or in any other form suitable for later analysis.

At step 304, the process receives one or more other values of physiological metrics or parameters. In an embodiment, values at step 304 are received through one or more other sensors 206 and may include, for example, values for one or more vital signs such as pulse, blood pressure, oxygenation, etc.

At step 306, the process performs a physiological analysis of the data that was received at steps 302, 304. Step 306 may include determining trend values ("increasing," "decreasing," etc.) based on prior measurements from the same device, or whether the current magnitude of a particular value has crossed a particular threshold that is associated with a particular physiological condition or change or is associated with a particular qualitative or quantitative descriptor or condition, for example, "elevated", "normal", "baseline", "exceptional," "average," "severe," etc.

At step 306, the process generates one or more recommendations for changes in behavior, activity, or treatment. Recommendations may comprise reports or protocols and may be based on stored tables that map the values obtained at step 302, step 304 to particular recommendations, reports, or protocols. Step 306 also may include computation such as determining whether a particular value is greater or less than values stored in the tables, and/or comparing particular trend values to corresponding trend indicators stored in the tables. Data representations other than tables may be used.

OVERVIEW OF EXAMPLE USES

For the purposes of illustrating clear examples, in various embodiments, the wireless or mobile measurement device 202 described herein may be used in one or more of the following ways. The examples refer to certain input parameters, algorithms and resulting recommendations. In one embodiment, each algorithm may be implemented using one or more computer programs or other software elements, or other computer logic, and may implement the clinical state of the art reflecting the current standard of care. However, unlike past approaches, each algorithm receives as an input at least one element of digital vascular waveform data. Thus, the approaches herein can use vascular analysis as a contributing parameter in determining a resulting recommendation. Further, the integration of vascular analysis data means that a healthcare provider can correlate the other parameter values to the vascular data to result in a better assessment of the overall health of the individual, or to provide a better clinical judgment of responsive treatment that should be considered.

In particular, an improvement provided herein is in the contribution of vascular analysis data, obtained for example from a bidirectional Doppler ultrasound measurement of the peripheral arteries, in a health assessment with other biomedical parameters. The vascular analysis data is usable in individuals who are in a health state or an unhealthy state, to recognize responses of the vasculature to the individual's health state, activity or environment. The vascular analysis data may be used to recommend personal interventions and determine how other parameter values, or the responses or interventions, may be affecting vascular structure or performance. For example, the vascular analysis data might indicate only two instances of dynamic activities of arteries, which are reflected as two "bounces" in a waveform obtained from the vascular analysis. The vascular analysis data also might indicate particular values or changes in the width(s) of waveform(s) and/or the velocity of waveform(s). In response, a healthcare provider might recommend a relaxation exercise, breathing exercises, increasing hydration, specific aerobic exercises, and/or self-administer a supplement or medication. A subsequent vascular analysis performed shortly thereafter might reveal that the individual has achieved three (3) "bounces", indicating improved vascular performance resulting from the relaxation exercise or other intervention as stated above.

The vascular analysis data may be used in combination with other apparatus such as ultrasound units that measure heart chamber activity or blood flow measurement apparatus.

Alternatively, a clinician may observe that a subject individual has elevated body temperature arising, for example, from heat exhaustion. With the availability of the vascular analysis data for the individual in addition to body temperature data, the clinician may be able to observe the effect of heat exhaustion on the vascular system. Further, the accumulation of data values from all other parameters may help explain anomalies that are seen in the waveform reflecting the vascular analysis. The combination of the vascular analysis data with other parameter values therefore permits a better global assessment of the individual and a better explanation of the individual's vascular response.

1. Use of Mobile Measurement Device to Motivate Change from Sedentary Behavior

John, a sedentary individual, is sprawled upon the couch in his living room, wearing or using a mobile monitoring device.

Fortunately, in his view, his favorite television show has just begun. Based on data collected from the mobile monitoring device, John's first hour of enjoyable viewing corresponds to a reasonably normal vitality condition. However, after ingesting a rather fatty meal and continuous television viewing for three more hours, John's vitality signals begin to decline, as measured by the mobile measurement device 202 as follows:

| Parameters: | 1$^{st}$ Hour: | 4$^{th}$ Hour: |
|---|---|---|
| Blood Pressure | Normal | Elevated |
| Pulse | Normal | Elevated |
| Respiration | Normal | Elevated |
| Oxygenation | Normal | Decreased |
| Nitric Oxide | Normal | Increased |
| Doppler Vascular Waveform | Moderately Severe | More Severe |

The sensors 206 process these physical changes in real-time. During hour 4, John decides to connect his mobile measurement device 202 to his tablet computer (an example of host computer 220). In an embodiment, John couples a universal serial bus (USB) cable from his tablet computer to the mobile measurement device 202. The mobile measurement device 202 contains a diagnostic computer program, which is automatically downloaded to the tablet computer and begins running as part of standard USB connection operations. During execution, based on the amount of change that the sensors detected in the 3-hour period, the diagnostic program generates and displays a report (an example of recommendations 216) to recommend a beneficial change in life activity as follows:

Algorithm Implementation & Recommendation:
  1. 20 minute walking activity
  2. 8 fl oz. water consumption
  3. 2 tablet aspirin intake to relieve blood pressure
  4. Utilize inhaler to increase oxygenation In response, John ceases his laziness and follows the step by step process. He continues to use or wear the mobile measurement device 202, and then re-connects it to his tablet computer. The diagnostic program reports the following changes in metrics or parameters:

| Parameters: | Decline: | Ascent: |
|---|---|---|
| Blood Pressure | Elevated | Normal |
| Pulse | Elevated | Normal |
| Respiration | Elevated | Normal |
| Oxygenation | Decreased | Normal |
| Nitric Oxide | Increased | Normal |
| Waveform | More Severe | Baseline |

Results:
The individual's blood pressure steadily returns to normal after the intake of aspirin. The recommended use of an inhaler returns his Oxygenation and Nitric Oxide levels to stable. Drinking water decreases the flow viscosity in his vascular system. Most importantly, the waveform velocity reaches its healthy baseline value.

2. Use of Mobile Measurement Device in Hospital Intensive Care Unit (ICU)

John was recently been admitted to the ICU. Upon arrival, healthcare providers are perplexed by John's symptoms. However, for the past day, John had been using his mobile measurement device 202 and has it with him. One of the healthcare providers connects the mobile measurement device 202 to a host computer 220 in the ICU, downloads or streams data from the mobile measurement device, and uses program logic on the host computer to generate a report of the following historical parameter values that the mobile measurement device had captured:

| Parameters: | 5 hrs prior to Arrival: | Point of Arrival: |
|---|---|---|
| Blood Pressure | Normal | Major Drop |
| Nitric Oxide | Normal | Normal |
| Respiration | Normal | Increasing |
| Temperature | Normal | Increasing |
| Pulse | Normal | Increasing |
| Waveform | Baseline | Increasing Velocity |

Based on the collected data, the host program provides the following recommendation:

Algorithm Assessment:
  1. Body Inflammatory State
  2. Potential Diagnosis: Sepsis

| Action | Skin infection diagnosis and treatment. Perform blood cultures. Increase antibiotics. |
|---|---|

The healthcare provider evaluates the assessment and recommended action, and decides to perform the recommended actions. As a result, the following physiological effects are observed:

Results:
Patient temperature returns to normal. Nitric oxide returns to normal. Pulse returns to normal. Blood Pressure becomes normalized. Temperature cools down. Waveform velocity returns to normal.

3. Use of Mobile Measurement Device in Athletics

Alice, marathon runner, regularly uses her mobile measurement device 202, which stores a data file indicating the following baseline parameters and goals:

| Parameters: | Baseline: | Goal: |
|---|---|---|
| Weight | Average | Exceptional |
| Blood Pressure | Average | Above Average |
| Pulse | Average | Above Average |
| Respiration | Average | Above Average |
| Nitric Oxide | Average | Exceptional |
| Oxygen | Average | Exceptional |
| Waveform | Average | Exceptional |

Over a training period of six months, Alice periodically downloads data from her mobile measurement device 202 to her laptop computer and reviews the data using program logic on the laptop. The program logic reports that, based on the data from the mobile measurement device, her body has met her goals. She is now prepared for the big race.

During the marathon, Alice continues to use her mobile measurement device 202. The mobile measurement device 202 comprises a near-field radio transceiver 230, such as a Bluetooth transceiver, that communicates with host computers having compatible transceivers that are located at waypoints on the race route. At various waypoints, Alice's team members, healthcare providers or race officials download data from Alice's mobile measurement device 202 to laptop computers at the waypoints. Host programs on the laptop computers periodically generate reports of Alice's performance. Additionally or alternatively, the mobile measurement device 202 comprises internal program logic that can display, on a wrist-mounted display, eyewear-mounted display or other output device 240, a brief report or indication of the following results. In either alternative, the vitality sensors remain intact to ensure Alice's physical condition is suitable to continue racing:

| Distance: | Health: |
|---|---|
| 1$^{st}$ Mile | Ok |
| 2$^{nd}$ Mile | Ok |
| 3$^{rd}$ Mile | Ok |
| 4$^{th}$ Mile | Ok |
| 5$^{th}$ Mile | Decline |

| Parameters: | Status: |
|---|---|
| Blood Pressure | Dropped below baseline |
| Pulse | Slight Increase |
| Body Temperature | Slight Increase |
| Waveform | Slight Increase |

Algorithm Assessment:
   1. Individual's bodily temperature increased
   2. Blood pressure is dropping
   3. Pulse is increasing
Algorithm Recommendation:
Subject is tending towards dehydration. Take more time at water stations. Consume more carbohydrates to replenish energy. Resume Running and decrease rate of pace slightly.

In this example, one or more of the values indicated above for Health, Status, Algorithm Assessment and Algorithm Recommendation may be represented in stored data that is maintained in the mobile measurement device 202, but not displayed or reported to Alice. Alternatively, one or more of the metrics may be reported to Alice or using the laptop computer at the waypoints; the alternatives are design choices that may depend, for example, on the size of display that is available on Alice's device. For example, if Alice is using a wrist-mounted computer or other output device 240 that has a liquid crystal display (LCD) having limited display capability, then the metrics may be reported in more limited form. Alternatively, if Alice's mobile measurement device 202 comprises a smartphone with a high-resolution color graphics display 250, then more elaborate reporting may be provided.

Continuing with the example, assume that Alice takes heed of the recommendations of the mobile measurement device 202 and changes her running behavior. Thereafter, the mobile measurement device 202 collects data indicating the following:

| Distance: | Health: |
|---|---|
| 6$^{th}$ Mile | Improved! |
| 7$^{th}$ Mile | Ok |
| 8$^{th}$ Mile | Ok |
| 9$^{th}$ Mile | Ok |
| 10$^{th}$ Mile | Ok |

Algorithm Assessment:
   1. Vital signs are normal and stable
   2. Body is adequately hydrated
Algorithm Recommendation
The body may continue further exertion!

Alice continues to review reports or indications from her mobile measurement device 202 as she enters later stages of the race. The mobile measurement device 202 collects data indicating the following:

| Distance: | Health: |
|---|---|
| 11$^{th}$ Mile | Ok |
| 12$^{th}$ Mile | Ok |
| 13$^{th}$ Mile | Ok |
| 14$^{th}$ Mile | Ok |
| 15$^{th}$ Mile | Ok |
| 16$^{th}$ Mile | Ok |
| 17$^{th}$ Mile | Ok |
| 18$^{th}$ Mile | Declining |
| 19$^{th}$ Mile | Declining |
| 20$^{th}$ Mile | Sharp Decline |

Algorithm Assessment:
   1. Health parameters started falling after the 18$^{th}$ Mile.
   2. Experienced a sharp decline after the 20$^{th}$ Mile.
   3. Further analysis of parameters required:

| Parameters: | 18$^{th}$ Mile: | 20$^{th}$ Mile |
|---|---|---|
| Blood Pressure | Moderate | Severe |
| Pulse | Moderate | Severe |
| Respiration | Moderate | Severe |
| Body Temperature | Moderate | Severe |
| Waveform | Moderate | Severe |
| Ambient Temperature | Sharp decrease in humidity | |

Algorithm Assessment:
   1. All Parameters are experiencing a sharp decline.
   2. Further Decline is hazardous.
   3. Individual is severely dehydrated.
Algorithm Recommendation:
   1. Halt running immediately.
   2. Consume water and carbs to replenish body.
   3. Continue walking until vitality signals increase.
Results:
Because it was much hotter towards the end of the race, our athlete experienced severe dehydration at her 20$^{th}$ mile. Without her vitality sensors, there would be no way to accurately determine her state of condition and hydration.

In each of the preceding examples, the metric "Waveform" represents data obtained from at least one vascular sensor 206 and is based on bidirectional waveform analysis. "Bidirectional" refers to the fact that in normal circulation, blood is pumped and flows in a first direction through a blood vessel, then briefly reverses direction, and then is pumped and flows again in the first direction. For example, a miniaturized Doppler vascular sensor may be used as one of the sensors 206 to generate and store data representing an acoustic waveform based on detecting the flow of blood in one or more blood vessels. This data is indicative of the elasticity of the blood vessels, among other metrics; for example, a wider waveform is observed to indicate greater elasticity of the walls of the blood vessels, larger volume of blood flow, or a thinner waveform is observed to indicate lesser volume and less elasticity, at least at the measurement site, and greater elasticity is associated with reduced risk of certain major diseases such as CVD, diabetes and respiratory ailments. Through data collection, observation of velocity and volume of waveform of the first, second, third, and sometimes a fourth waveform, the processes herein will be able to correlate more accurately the status of physiological responses. The inventor fundamentally has recognized that combining vascular function information 211 representing vascular condition with one or more other physiological metrics 212 will provide a better capability for evaluating overall health of an individual and for providing recommendations for activity or treatment. Further, the integration of vascular bidirectional waveform analysis data representing vascular condition with a plurality of other physiological metrics will provide a superior capability for evaluating overall health of an individual and for providing recommendations for activity or treatment. Still further, having multiple examples of vascular data available over a long period of time can provide better environmental information on which health assessments may be based. Moreover, the vascular data is expected to indicate, relate to, represent or be proportional to the relative condition of the endothelium, a thin layer of cells that lines the interior of vascular vessels. Its condition or other indicators derived from the vascular data are believed to represent one or more factors or variables that are independent with respect to contribution to the onset of vascular disease and/or an independent contributing factor in the onset or occurrence of atherosclerosis or myocardial infarction.

Figure 4:
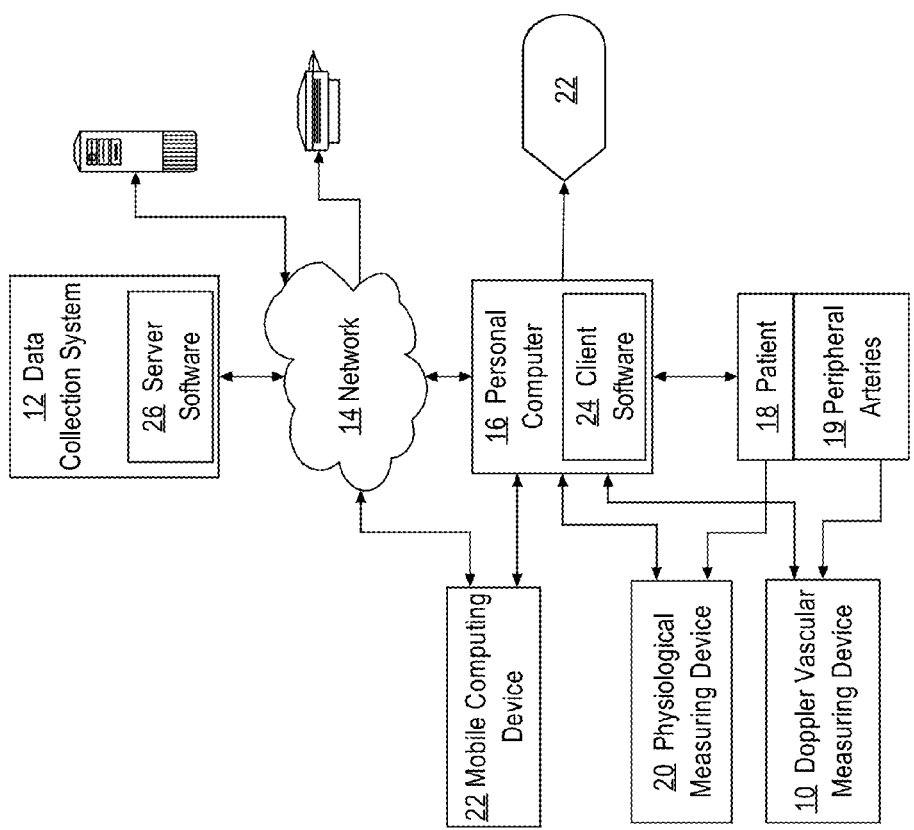
FIG. 4 illustrates a networked physiological measurement system in one example implementation.

Physiological Measurement System and Methods Featuring Doppler Vascular Measurement FIG. 4 illustrates a networked physiological measurement system in one example implementation.

The elements of FIG. 4 may be located entirely in a clinical setting such as a physician's office, or located in whole or in part with a patient.

In an embodiment, data collection system 12 is a computer that interfaces to network 14 and hosts server software 26 to receive and store signals and patient measurements and to perform analysis logic. Data collection system 12 typically comprises a laptop computer or other portable computing device that can be moved to different treatment rooms where patients are located, but the data collection system also could be a physician's home computer or multiple computers at a data center. Server software 26 consists of control programs that generally enable a physician to review measurements obtained from the Doppler system that is further described herein, or other data sources, and/or to review a complete electronic patient chart or record that includes historical vital signs measurements, records of interventions and medications, and other data. In one approach, electronic patient charts and the server software 26 are hosted on a separate server computer that is connected to network 14. The data collection system 12 can be periodically connected to or disconnected from the network 14 depending on clinical needs.

The local network 14 may include a printer or other output devices for printing reports or other materials for physician or staff use.

A personal computer 16 is connected to the local network 14 and includes client software 24 and a display unit 22 that are accessible to a patient 18. In a typical deployment the provider's office includes a kiosk, carrel, viewing room, or other private or semi-private area in which the patient 18 can access the personal computer 16 and view or interact with modules from the module library 30. Alternatively the personal computer 16 may be located at a patient's home or business. The computer 16 may include a sound card, headphones, speakers or other audio output units.

A Doppler system 10 is connected to the personal computer 16 and comprises sensors that are placed preferably on the peripheral arteries 19 of the patient 18. Peripheral arteries 19 may be at the ankles, wrists, or other peripheral locations of the body of the patient. In an embodiment, the Doppler system 10 has sensors that can be temporarily attached to the feet and ankles of a patient to acoustically detect pulses of the bloodstream in the circulatory system of the patient. The Doppler system 10 may include stored programs for generating and storing data representing signal waveforms derived from the acoustic measurements. Typically the data indicates the velocity of the bloodstream, at a particular measurement point in the vascular system, over time. An example is a modification of V-link software commercially available from Koven Technology Inc., Saint Louis, Mo., but other programs may be used.

The patient 18 also may own or have access to a mobile computing device 22, which may comprise a tablet computer, smartphone or laptop that transports with the patient to various locations. In such an embodiment, one or both of the Doppler system 10 and physiological measuring device 20 may interface to the mobile computing device 22, rather than to personal computer 16, or to both. For example, the Doppler system 10 and physiological measuring device 20 may have wireless networking interfaces that can communicate through a wireless access point to the personal computer 16 or through network 14 to data collection system 12.

The patient 18 may provide additional personal health data to the data collection system 12 in the form of data, files, or images that are stored on or obtained using a physiological measuring device 20. For example, in some cases a patient 18 may perform measurements of blood pressure, pulse, respiration rate, temperature, or other data at home using instruments or measurement devices, store the measurements or data on the physiological measuring device 20, and bring the device to the provider's office at the time of an office visit. Additionally or alternatively, client software 24 may facilitate communicating data from one or both of the Doppler system 10 and device 20 to personal computer 16 and to data collection system 12.

The provider's office may include any number of additional computers that are networked using local network 14 for the purpose of entering measurements, chart data, vital signs, or other health information. For example, each workstation, examining room or other station of the provider's office may include a terminal or computer at which medical staff can enter data into the electronic patient chart for a particular patient. In some deployments the additional computers may consist of portable digital assistants, other portable computers, barcode readers, and other portable data entry or data viewing devices that are connected to the local network 14 using wireless signals and protocols.

Using this arrangement, the physician can collect and review a variety of patient-generated data and office-generated data including Doppler vascular data. Based on the data, the physician can select and provide each patient with a customized version of one or more reports or. The version provided to the patient is customized in relation to that particular patient's specific condition, pathology, physiology, personality, goals or treatment plan.

For example, the physician examining a significantly overweight patient may determine that the patient could benefit from detailed, patient-customized education relating to diabetes. At the time of an office visit or at another time, and while working with server software 26 at the data collection system 12 or another networked computer in the office and viewing an electronic patient chart for that patient, the physician would select a diabetes module from a list of modules in a module library. The physician would also customize the module for presentation to this particular patient in several ways. First, the physician can select one or more parameters of the module by interacting with a graphical user interface and program logic provided as part of the server software. Second, the physician can receive selections of module parameters that are determined automatically by the server software 26 based on the stored values in the electronic patient chart for the present patient.

Network 14 broadly represents one or more local networks, wide area networks, internetworks or internets using wire line, wireless, terrestrial or satellite links.

In an embodiment, server software 26 implements a service that uses various bodily measures or parameters, such as vital signs, blood glucose, gases in body, respiratory activity, exercise, nutrition and vascular function, to help achieve better vascular and overall health. The parameters may be measured automatically via wireless devices or mobile apps, or manually. Measurement using wireless devices may include receiving input from Withings' wireless scale, Withings' blood pressure monitor, Fitbit's activity monitor, or the Doppler system 10. Measurement using mobile apps may include receiving data apps hosted on mobile computing device 22, such as Heart Pal to record blood pressure and heart rate, Livestrong Calorie Tracker to record food intake and exercise, Daily Burn to scan bar codes of food items, and/or Mint Nutrition to get restaurant food nutritional information.

Obtaining patient data manually may occur through medical office visits at which test result data is collected using Doppler ultrasound measurements, laboratory tests, patient medical history and physical exams, or other sources. Obtaining patient data manually may occur through recording patient data values using at-home or other field equipment such as personally recorded data for diet and exercise routines, at-home scales, at-home blood pressure cuffs, at-home sphygmomanometers, or other devices.

In an embodiment, server software 26 is configured to generate and provide one or more interpretations of data that has been collected from devices 10, 20 via computers 16, 22. The interpretations of data may be provided in any of several forms including reports, animations, and figures. Reports may include text or graphical reports that relate to patient health in relation to hypertension, obesity, diabetes, cardiovascular disease, or other issues.

Animations may include 2-dimensional or 3-dimensional representations of the blood flow in the arteries of the patient 18 with varying degrees of plaque formation and/or varying constituents such as fatty acid, glucose, or others. Animations may also depict blood flow across the whole body. Animations may be representative, rather than specific. That is, rather than attempting to accurately depict exactly the interior condition of the vascular system of the patient 18, which cannot be known with certainty, the animations may have the same general graphic appearance for every patient but may illustrate different degrees of plaque formation or other constituents that the server software 26 has inferred based on analysis of the measured data from the patient 18.

Figures may include a graphical image of a typical body image for the patient based on the patient's actual height, weight, age and sex data. In an embodiment, data received from patient 18 may include a digital image of the patient and server software 26 is configured to modify and re-render the digital image to illustrate that patient's ideal body image or a goal image.

In an embodiment, server software 26 is configured to provide educational information such as one or more explanations of interpretations of the data that has been received from the patient 18.

In an embodiment, server software 26 is configured to provide one or more real time recommendations for the patient 18, dependent on the health status of the patient. For example, in various embodiments the recommendations may include:

Protocols for nutrition
Protocols for exercise
Protocols for sports performance
Protocols for patient lifestyle or changes
Protocols for stress management
Protocols for patient lifestyle or changes
Protocols for supplements/medications In an embodiment, server software 26 is configured to record and track progress of the patient 18 with respect to one or more health metrics. Recording and tracking progress can involve using one or more devices or apps to repeatedly record parameters mentioned in real time, or close in time, or received through periodic inputs or uploads from the user. Recording and tracking progress also can involve creating and storing one or more journals, charts and figures that compile or consolidate patient data to allow the patient to track progress.

In an embodiment, server software 26 is configured to provide one or more reminders to the patient 18 to encourage continual engagement with the processes and systems that are described herein. In various embodiments, reminders may comprise any of notifications messages, alarms, and/or calendar reminders.

In an embodiment, server software 26 is configured to provide an interface between a physician and a user such as patient 18. In an embodiment, server software 26 is configured to allow a physician to access data from patient 18 either using a terminal or computer to connect to data collection system 12 or to receive emails of data from the patient. In an embodiment, server software 26 is configured to allow the physician to relay messages to the patient. Examples of messages from physician to patient 18 may include positive feedback, negative feedback, scheduling appointments, and scheduling interventions.

In an embodiment, server software 26 is configured to provide an interface between the clinical setting and a non-clinical setting. For example, by storing and managing patient 18, the server software 26 makes the patient data available for easy access at hospitals, medical offices, clinics or other locations.

In an embodiment, server software 26 is configured to provide social forums. Examples of social forums include patient to patient communication. Anonymity may be allowed and non-disclosure agreements may be enforced. In an embodiment, physicians may provide input in the social forums also.

The system as described has numerous uses and applications. A first set of applications are facilitated by using one or both of the devices 10, 20 on the peripheral arterial system, whether on the ankle, the arm, or the wrist, as well as neck, chest or other sites in the body. Applications and scenarios may include people with heart failure; people with cardiac myopathy; people with cardiac hypertrophy; athletes that have enlarged hearts, whether physiological or pathological; patients with ventricular assisted devices. In the case of the latter, typical patients are people with heart failure who are not able to have a heart transplant, and instead use ventricular assisted devices to improve blood flow; the use of Doppler system 10 enables the server software 26 to help assess circulation and assist in medical treatment or lifestyle treatment.

In an embodiment, server software 26 is configured to support analysis of cardiac arrhythmias. In one approach, medical centers have used Doppler evaluation of the pulmonary artery. However, it is difficult to evaluate pulmonary artery function in terms of elasticity and velocity, and what effects it is having during arrhythmias or atrial fibrillation, using Doppler because the lungs lie between the exterior sensor and the pulmonary artery, and therefore the air contained in the lungs has to be taken into account in evaluating the Doppler signals or signature. The use of peripheral sites such as the wrist, arm, or ankles will be more accurate, and has fewer challenges for interpretation of the resulting data. Further, as data is accumulated, the data can be used to see changes before arrhythmias occur, and thus the physician will have the opportunity to initiate intervention before the onset of arrhythmia. Moreover, the physician may be able to perform further analysis based on data from Doppler system 10 to modify treatment after the arrhythmia. That information will help to monitor hemodynamics even while an arrhythmia is occurring.

In an embodiment, server software 26 is configured to support analysis for sports medicine using biomarkers and biosensors and waveform analysis to provide recommendations and provide performance status of athletes.

In an embodiment, server software 26 is configured to use waveform analysis based on input from Doppler system 10 to form and report associations with changes in electrocardiography (EKG) data. With time, changes in waveforms seen via data from Doppler system 10 may show a correlation with wave changes that occur on the EKG/ECG, specifically the P wave, T wave and QRS complex, and the changes on voltages. Changes in EKG/ECG waveforms are important in assessing cardiac function, and the use of Doppler in the periphery will add to the understanding of those EKG changes over time.

In an embodiment, server software 26 is configured to assess changes in physiology that occur during conditions of athletic stress. For example, deaths continue to occur on the basketball court and playing fields in other sports, at all levels. Analysis of data from Doppler system 10 may be used to detect or assess vagal stimulation or early repolarization changes, which are usually noted through EKG data; the Doppler system 10 may also provide assessing information when an EKG may not be feasible.

In an embodiment, server software 26 is configured to detect and generate reports or assessments about cardiac irregularities such as unusual rhythms, extra beats or premature ventricular contractions. In an embodiment, server software 26 is configured to use a peripheral bi-directional Doppler analysis based on data from Doppler system 10 to assess hemodynamics.

To be clear, the hypertrophic heart or enlarged heart is a major health concern when detected, especially for athletes. EKG changes may be used as a means of detection, but past approaches have not used peripheral vascular correlation to try to understand when this diagnosis or condition needs to be better addressed and treated differently or more aggressively.

In an embodiment, server software 26 is configured to provide assessments in support of genetic testing for hypertrophy problems. The application of a vascular study on a daily basis can help answer questions of EKG changes during physiological or pathological states of hypertrophy.

Figure 5:
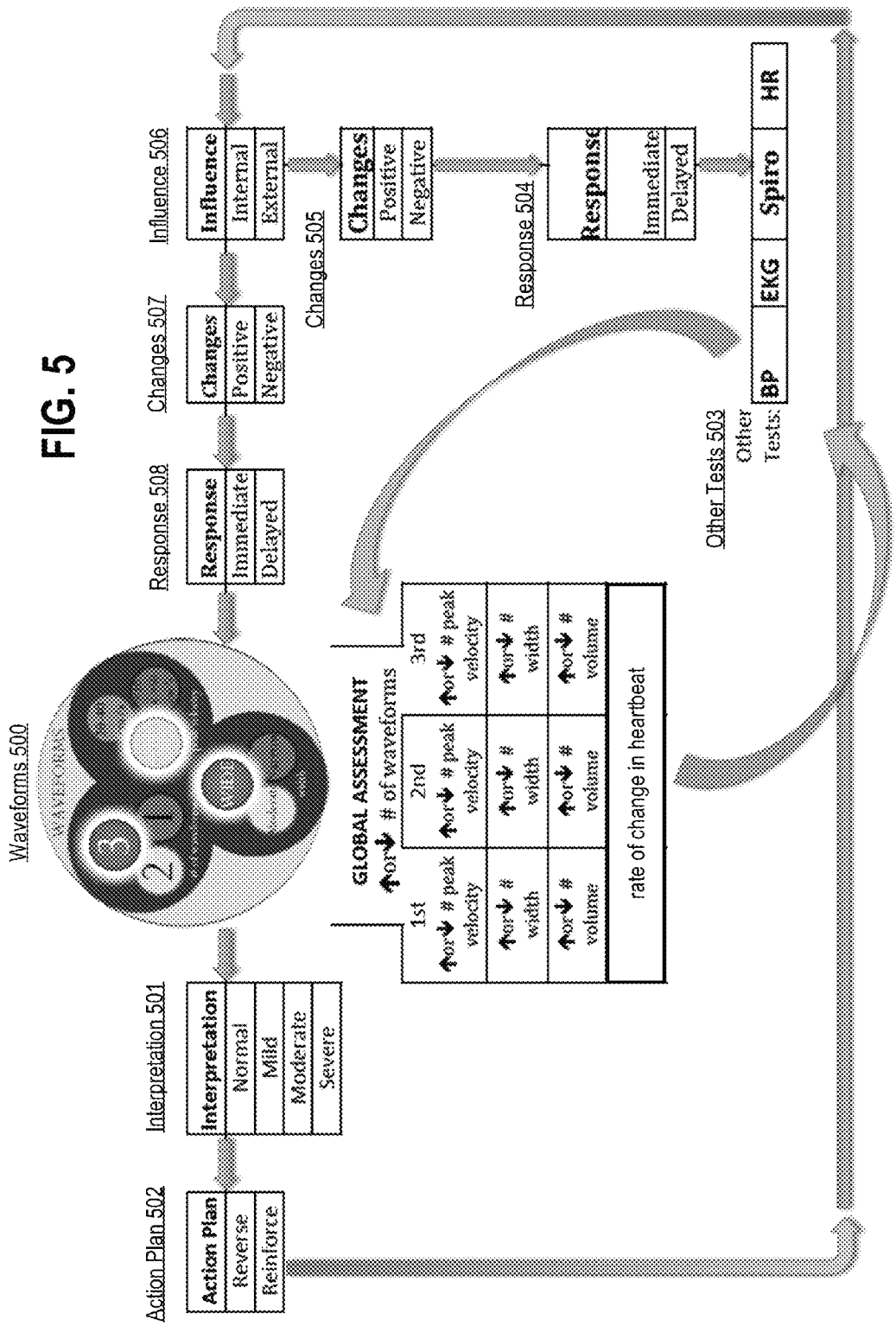
FIG. 5 illustrates data flows in example processes of performing a global assessment of health with correlations of various data sources and sensors relating to vascular systems.

FIG. 5 illustrates data flows in example processes of performing a global assessment of health with correlations of various data sources and sensors relating to vascular systems.

Referring to FIG. 5, a process of determining a global assessment of health using the devices, sensors and data sources described herein may have one or more elements of internal influence and external influence 506. Influence 506, internal is equivalent to biological sensors such as vital signs, oxygenation, glucose, nitric oxide, etc. Influence 506, external reflects environmental factors such as running a race, exertion, anxiety, stress, or occupational exposure such as that seen in firefighters.

These influences lead to physiological changes 505, 507, which may be positive or negative depending on the influence 506.

A response 504, 508 is a biological result of the changes 505, 507 and may be Immediate or Delayed. For example the nervous system is structured for Immediate response 504, 508 to changes 505, 507 to cause increase in oxygenation or another biological effect. An example of a Delayed response 504, 508 is the release of hormones and their effects. An example of Immediate response 504, 508 is production of nitric oxide as a result of exercise. An example of Delayed response 504, 508 is from the immune system.

Three waveforms 500 typically are possible and degrees of the waveforms are observed. Vascular measurement involves determining whether one, two or three waveforms 500 are present. There could be intermediate phases or steps that occur as the body transitions from one waveform type to the next, so it may be unclear whether two or three waveforms 500 are represented. Velocity may have green (average to normal) range for the first waveform. Normal velocity for the $2^{nd}$, $3^{rd}$, $4^{th}$ waveform is not known, as there is no known research on it. Width or space between waveforms 500 (or periodicity) indicates relative vascular health; as vascular health improves, waveforms 500 get wider.

The data leads to an interpretation 501 of Normal, Mild, Moderate or Severe plaque formation or occlusion of the cardiovascular arteries.

Various embodiments allow more precision as to the degrees of these four categories, degrees of Moderate for example. Various embodiments are configured to measure degrees of velocity not just of the $1^{st}$ waveform but all the waveforms 500 and the widths.

Interpretation 501 leads to an action plan 502 which may take the form as disclosed in the preceding sections of recommendations, reports and/or protocols.

Units of measurement from other tests 503 in various embodiments from blood pressure, EKG, spirometry, heart rate yield data over time associated with changes 505, 507 and responses 504, 508 and how the measured values relate to the vascular measurements. Patterns can be deduced and associated with the individual's vascular response.

Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 1:
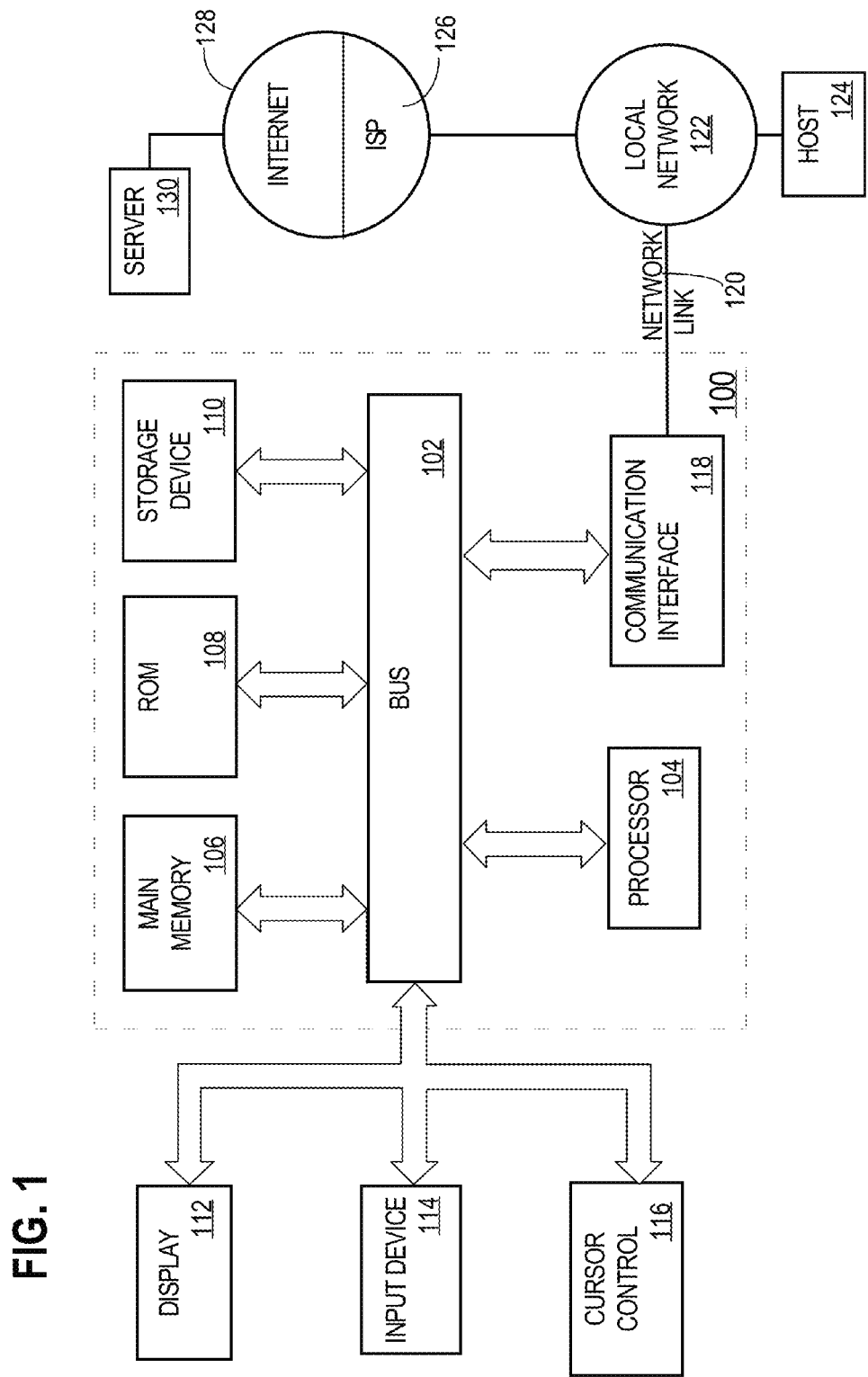
FIG. 1 is a block diagram that illustrates a computer system upon which an embodiment of the invention may be implemented.

For example, FIG. 1 is a block diagram that illustrates a computer system 100 upon which an embodiment of the invention may be implemented.

Computer system 100 includes a bus 102 or other communication mechanism for communicating information, and a hardware processor 104 coupled with bus 102 for processing information. Hardware processor 104 may be, for example, a general purpose microprocessor.

Computer system 100 also includes a main memory 106, such as a random access memory (RAM) or other dynamic storage device, coupled to bus 102 for storing information and instructions to be executed by processor 104. Main memory 106 also may be used for storing temporary variables or other intermediate information during execution of instructions to be executed by processor 104. Such instructions, when stored in non-transitory storage media accessible to processor 104, render computer system 100 into a special-purpose machine that is customized to perform the operations specified in the instructions.

Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT), for displaying information to a computer user. An input device 114, including alphanumeric and other keys, is coupled to bus 102 for communicating information and command selections to processor 104. Another type of user input device is cursor control 116, such as a mouse, a trackball, or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Computer system 100 may implement the techniques described herein using customized hard-wired logic, one or more ASICs or FPGAs, firmware and/or program logic which in combination with the computer system causes or programs computer system 100 to be a special-purpose machine. According to one embodiment, the techniques herein are performed by computer system 100 in response to processor 104 executing one or more sequences of one or more instructions contained in main memory 106. Such instructions may be read into main memory 106 from another storage medium, such as storage device 110. Execution of the sequences of instructions contained in main memory 106 causes processor 104 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 110. Volatile media includes dynamic memory, such as main memory 106. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 102. Transmission media can also take the form of acoustic or light waves, such as those generated during radio-wave and infra-red data communications.

Various forms of media may be involved in carrying one or more sequences of one or more instructions to processor 104 for execution. For example, the instructions may initially be carried on a magnetic disk or solid state drive of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector can receive the data carried in the infra-red signal and appropriate circuitry can place the data on bus 102. Bus 102 carries the data to main memory 106, from which processor 104 retrieves and executes the instructions. The instructions received by main memory 106 may optionally be stored on storage device 110 either before or after execution by processor 104.

Computer system 100 also includes a communication interface 118 coupled to bus 102. Communication interface 118 provides a two-way data communication coupling to a network link 120 that is connected to a local network 122. For example, communication interface 118 may be an integrated services digital network (ISDN) card, cable modem, satellite modem, or a modem to provide a data communication connection to a corresponding type of telephone line. As another example, communication interface 118 may be a local area network (LAN) card to provide a data communication connection to a compatible LAN. Wireless links may also be implemented. In any such implementation, communication interface 118 sends and receives electrical, electromagnetic or optical signals that carry digital data streams representing various types of information.

Network link 120 typically provides data communication through one or more networks to other data devices. For example, network link 120 may provide a connection through local network 122 to a host computer 124 or to data equipment operated by an Internet Service Provider (ISP) 126. ISP 126 in turn provides data communication services through the world wide packet data communication network now commonly referred to as the "Internet" 128. Local network 122 and Internet 128 both use electrical, electromagnetic or optical signals that carry digital data streams. The signals through the various networks and the signals on network link 120 and through communication interface 118, which carry the digital data to and from computer system 100, are example forms of transmission media.

Computer system 100 can send messages and receive data, including program code, through the network(s), network link 120 and communication interface 118. In the Internet example, a server 130 might transmit a requested code for an application program through Internet 128, ISP 126, local network 122 and communication interface 118.

The received code may be executed by processor 104 as it is received, and/or stored in storage device 110, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:
1. A data processing method comprising:
receiving, from a portable physiological measuring device configured for temporary attachment to a human body, data representing a plurality of different physiological metrics or parameters of the body;

receiving, from one or more Doppler vascular sensors configured for temporary attachment to peripheral artery locations of the body and a portable Doppler vascular signal measuring device coupled to the Doppler vascular sensors, vascular function information for the body;

wherein receiving the vascular function information comprises receiving data based on bidirectional waveform Doppler ultrasound analysis that can measure or indicate an elasticity of one or more blood vessels;

determining medical condition data indicating one or more medical conditions of a patient based on analysis and correlations of the vascular function information and the one or more physiological metrics, wherein determining the medical condition data involves at least:

determining a number of waves represented in one or more vascular waveforms of the vascular function information or a change in a width or a velocity of one or more particular waves of the one or more vascular waveforms;

inputting the data representing the plurality of different physiological metrics or parameters of the body, and the vascular function information including the data based on bidirectional waveform Doppler ultrasound analysis that can measure or indicate an elasticity of one or more blood vessels, to a plurality of algorithms that are configured to correlate the data based on bidirectional waveform Doppler ultrasound analysis with the plurality of different physiological metrics or parameters of the body and to determine a recommendation of responsive treatment based upon a combination of both the vascular function information including the data based on bidirectional waveform Doppler ultrasound analysis and three or more of the plurality of different physiological metrics or parameters of the body selected from among: blood pressure, pulse, respiration, oxygenation, nitric oxide, body temperature, weight;

wherein the plurality of algorithms comprise: a first algorithm configured to detect an increase in severity of the vascular function information, a decrease in oxygenation, an increase in nitric oxide, and an elevation of blood pressure, pulse and respiration, and in response, to generate a first recommendation to a user of the portable physiological measuring device of intake of aspirin, use of an inhaler, and consumption of water; a second algorithm configured to detect severe increases in blood pressure, respiration, pulse, temperature and vascular waveform, and in response, to generate a second recommendation to a user of the portable physiological measuring device to cease exercise and consume water;

generating and providing output records specifying one or more of: recommendations for actions that an individual or healthcare provider should take in response to the recommendations or parameters; or one or more reports, animations or figures;

wherein the method is performed by one or more computing devices.

2. The method of claim 1 wherein the generating and providing comprises:
determining one or more positive changes or negative changes in the physiological metrics or parameters;
determining whether the changes indicate an immediate physiological response or a delayed physiological response;
determining an interpretation of severity of the changes, the response, and the one or more vascular waveforms;
forming an action plan based on the interpretation.

3. The method of claim 1 further comprising determining whether the number of waves represents an increase or decrease in the number of waves and, for each of the number of waves, one or more of: a change in blood velocity; a change in width of a wave; a change in blood volume; and a rate of change in heartbeat.

4. The method of claim 3 wherein the physiological metrics or parameters include at least one of blood pressure, EKG, spirometry.

5. The method of claim 1 wherein the one or more computing devices comprise any of: a smartphone; a tablet computer; a laptop computer or other personal computer; a workstation; a watch computer; a ring-mounted computer; an active steering wheel of a motor vehicle; a hat-mounted computer; a helmet-mounted computer; an eyewear-mounted computer.

6. The method of claim 1 wherein the vascular function information comprises or is based on the bidirectional waveform Doppler ultrasound analysis.

7. The method of claim 1 wherein receiving the physiological metrics or parameters comprises receiving from one or more of any of the following: an infrared, crystal technology, or light-based physiological monitor; a sensor configured for use with augmented reality technology; a sensor configured for use with auto-fluorescence technology; a blood pressure sensor; a pulse sensor; a respiratory rate sensor comprising, for example, one or more chest patches, wrist patches, and/or chest straps; a body temperature sensor; an oxygen absorption sensor; a carbon dioxide sensor; a nitric oxide sensor; a blood glucose sensor; a sensor of electrolytes, nutrients in a circulation, or other metrics; one or more contact lenses configured to measure capillary blood flow; a flow meter; a spirometer; a mouthpiece.

8. The method of claim 1 wherein the vascular function information provides metrics, reports, or values that indicate overall health attributes of blood vessels or other components of a vascular system, or particular attributes of blood vessels or other components of the vascular system.

9. The method of claim 1 wherein the output records comprise any of: a status report on vascular function; a list of options for medical intervention in the patient based on medical standards of practice based on one or more medical indications represented in the vascular function information; reports or recommendations suggesting sepsis, hypertension, hypotension, or respiratory dysfunction; a protocol for exercise; a protocol for sports performance; a protocol for patient lifestyle or changes in lifestyle; a protocol for patient stress management; a report of recommendations, or expected effects of, any of several aspects of treatment including but not limited to nutrition, exercise, supplements, and medications.

10. The method of claim 1 wherein the output records comprise any of: Protocols for disease intervention; Protocols for nutrition; Protocols for exercise; Protocols for sports performance; Protocols for patient lifestyle or changes; Protocols for stress management; Protocols for patient lifestyle or changes; Protocols for supplements/medications.

11. The method of claim 1 wherein the output records comprise assessments of vascular circulation based on stored indication data that correlates particular Doppler vascular signals with any one or more of heart failure, cardiac myopathy, cardiac hypertrophy; enlarged heart, or use of ventricular assisted devices.

12. The method of claim 1 wherein the output records comprise assessments of cardiac arrhythmia, extra beats or premature ventricular contractions.

13. The method of claim 1 wherein the physiological measuring device comprises an electrocardiogram (EKG) apparatus and wherein the correlation comprises correlating EKG data with Doppler vascular data.

14. The method of claim 1, wherein determining the medical condition data is performed by at least determining the number of waves represented in the one or more vascular waveforms of the vascular function information.

15. The method of claim 1, wherein the one or more Doppler vascular sensors configured for temporary attachment to one or more peripheral arteries located at an ankle of the body.

16. A non-transitory computer-readable medium comprising one or more sequences of instructions which when executed using one or more processors cause the one or more processors to perform:
receiving, from a portable physiological measuring device configured for temporary attachment to a human body, data representing a plurality of different physiological metrics or parameters of the body;
receiving, from one or more Doppler vascular sensors configured for temporary attachment to peripheral artery locations of the body and a portable Doppler vascular signal measuring device coupled to the Doppler vascular sensors, vascular function information for the body;
wherein receiving the vascular function information comprises receiving data based on bidirectional waveform Doppler ultrasound analysis that can measure or indicate an elasticity of one or more blood vessels;
determining medical condition data indicating one or more medical conditions of a patient based on analysis and correlations of the vascular function information and the one or more physiological metrics, wherein determining the medical condition data involves at least:
determining a number of waves represented in one or more vascular waveforms of the vascular function information or a change in a width or a velocity of one or more particular waves of the one or more vascular waveforms;
inputting the data representing the plurality of different physiological metrics or parameters of the body, and the vascular function information including the data based on bidirectional waveform Doppler ultrasound analysis that can measure or indicate an elasticity of one or more blood vessels, to a plurality of algorithms that are configured to correlate the data based on bidirectional waveform Doppler ultrasound analysis with the plurality of different physiological metrics or parameters of the body and to determine a recommendation of responsive treatment based upon a combination of both the vascular function information including the data based on bidirectional waveform Doppler ultrasound analysis and three or more of the plurality of different physiological metrics or parameters of the body selected from among: blood pressure, pulse, respiration, oxygenation, nitric oxide, body temperature, weight;
wherein the plurality of algorithms comprise: a first algorithm configured to detect an increase in severity of the vascular function information, a decrease in oxygenation, an increase in nitric oxide, and an elevation of blood pressure, pulse and respiration, and in response, to generate a first recommendation to a user of the portable physiological measuring device of intake of aspirin, use of an inhaler, and consumption of water; a second algorithm configured to detect severe increases in blood pressure, respiration, pulse, temperature and vascular waveform, and in response, to generate a second recommendation to a user of the portable physiological measuring device to cease exercise and consume water;
generating and providing output records specifying one or more of: recommendations for actions that an individual or healthcare provider should take in response to the recommendations or parameters; or one or more reports, animations or figures.

17. The non-transitory computer-readable medium of claim 16 wherein the sequences of instructions for generating and providing comprise sequences of instructions which when executed cause:
determining one or more positive changes or negative changes in the physiological metrics or parameters;
determining whether the changes indicate an immediate physiological response or a delayed physiological response;
determining an interpretation of severity of the changes, the response, and the one or more vascular waveforms;
forming an action plan based on the interpretation.

18. The non-transitory computer-readable medium of claim 16 further comprising sequences of instructions which when executed cause determining whether the number of waves represents an increase or decrease in the number of waves and, for each of the number of waves, one or more of: a change in blood velocity; a change in width of a wave; a change in blood volume; and a rate of change in heartbeat.

19. The non-transitory computer-readable medium of claim 18 wherein the physiological metrics or parameters include at least one of blood pressure, EKG, spirometry.

20. The non-transitory computer-readable medium of claim 16 wherein the one or more computing devices comprise any of: a smartphone; a tablet computer; a laptop computer or other personal computer; a workstation; a watch computer; a ring-mounted computer; an active steering wheel of a motor vehicle; a hat-mounted computer; a helmet-mounted computer; an eyewear-mounted computer.

21. The non-transitory computer-readable medium of claim 16 wherein the vascular function information comprises or is based on the bidirectional waveform Doppler ultrasound analysis.

22. The non-transitory computer-readable medium of claim 16 wherein receiving the physiological metrics or parameters comprises receiving from one or more of any of the following: an infrared, crystal technology, or light-based physiological monitor; a sensor configured for use with augmented reality technology; a sensor configured for use with auto-fluorescence technology; a blood pressure sensor; a pulse sensor; a respiratory rate sensor comprising, for example, one or more chest patches, wrist patches, and/or chest straps; a body temperature sensor; an oxygen absorption sensor; a carbon dioxide sensor; a nitric oxide sensor; a blood glucose sensor; a sensor of electrolytes, nutrients in a circulation, or other metrics; one or more contact lenses configured to measure capillary blood flow; a flow meter; a spirometer; a mouthpiece.

23. The non-transitory computer-readable medium of claim 16 wherein the vascular function information provides metrics, reports, or values that indicate overall health attributes of blood vessels or other components of a vascular system, or particular attributes of blood vessels or other components of the vascular system.

24. The non-transitory computer-readable medium of claim 16 wherein the output records comprise any of: a status report on vascular function; a list of options for medical intervention in the patient based on medical standards of practice based on one or more medical indications represented in the vascular function information; reports or recommendations suggesting sepsis, hypertension, hypotension, or respiratory dysfunction; a protocol for exercise; a protocol for sports performance; a protocol for patient lifestyle or changes in lifestyle; a protocol for patient stress management; a report of recommendations, or expected effects of, any of several aspects of treatment including but not limited to nutrition, exercise, supplements, and medications.

25. The non-transitory computer-readable medium of claim 16 wherein the output records comprise any of: Protocols for disease intervention; Protocols for nutrition; Protocols for exercise; Protocols for sports performance; Protocols for patient lifestyle or changes; Protocols for stress management; Protocols for patient lifestyle or changes; Protocols for supplements or medications.

26. The non-transitory computer-readable medium of claim 16 wherein the output records comprise assessments of vascular circulation based on stored indication data that correlates particular Doppler vascular signals with any one or more of heart failure, cardiac myopathy, cardiac hypertrophy; enlarged heart, or use of ventricular assisted devices.

27. The non-transitory computer-readable medium of claim 16 wherein the output records comprise assessments of cardiac arrhythmia, extra beats or premature ventricular contractions.

28. The non-transitory computer-readable medium of claim 16 wherein the physiological measuring device comprises an electrocardiogram (EKG) apparatus and wherein the correlation comprises correlating EKG data with Doppler vascular data.

29. The non-transitory computer-readable medium of claim 16 wherein determining the medical condition data is performed by at least determining the number of waves represented in the one or more vascular waveforms of the vascular function information.

30. The non-transitory computer-readable medium of claim 16, wherein the one or more Doppler vascular sensors configured for temporary attachment to one or more peripheral arteries located at an ankle of the body.

\* \* \* \* \*